United States Patent
Lomax (10) Patent No.: US 8,461,559 B2
(45) Date of Patent: Jun. 11, 2013

(54) METHOD FOR EVALUATING RADIATION MODEL DATA IN PARTICLE BEAM RADIATION APPLICATIONS

(75) Inventor: Antony Lomax, Windisch (CH)

(73) Assignee: Paul Scherrer Institut, Villigen PSI (CH)

( * ) Notice: Subject to any disclaimer, the term of this patent is extended or adjusted under 35 U.S.C. 154(b) by 0 days.

(21) Appl. No.: 13/257,408

(22) PCT Filed: Jan. 8, 2010

(86) PCT No.: PCT/EP2010/050157
§ 371 (c)(1),
(2), (4) Date: Sep. 28, 2010

(87) PCT Pub. No.: WO2010/105858
PCT Pub. Date: Sep. 23, 2010

(65) Prior Publication Data
US 2012/0056109 A1    Mar. 8, 2012

(30) Foreign Application Priority Data
Mar. 17, 2009  (EP) .................................. 09155320

(51) Int. Cl.
  *B01J 19/12*  (2006.01)
(52) U.S. Cl.
  USPC ................ 250/492.3; 250/492.1; 250/492.21; 315/500; 315/502; 315/505; 378/65
(58) Field of Classification Search
  USPC .............. 250/492.1, 492.21, 492.22, 492.23, 250/492.3; 315/500, 502–505; 378/65
  See application file for complete search history.

(56) References Cited

U.S. PATENT DOCUMENTS

| 6,338,548 | B1 | 1/2002 | Silverbrook |
| 7,348,579 | B2 | 3/2008 | Pedroni |

(Continued)

FOREIGN PATENT DOCUMENTS

| EP | 1584353 A1 | 10/2005 |
| EP | 1900392 A1 | 3/2008 |

(Continued)

OTHER PUBLICATIONS

Jaekel, et al: "Treatment Planning for Heavy Ion Irradiation", Physica Medica, vol. XIV, Supplement 1, 6th Workshop on Heavy Charged Particles in Biology and Medicine, XP000908768, Jul. 1998, pp. 53-62, Darmstadt, Germany.

(Continued)

*Primary Examiner* — Bernard E Souw
(74) *Attorney, Agent, or Firm* — Laurence A. Greenberg; Werner H. Stemer; Ralph E. Locher (57) ABSTRACT

A method for evaluating radiation model data in particle beam radiation applications, in particular in proton beam therapy of a determined target volume of malignant tissue within a patient, includes the following steps: a) gaining diagnostic data for a determined target volume to be irradiated; b) calculating a particle range in the predetermined target volume based on the diagnostic data for the determined target volume; c) designing a radiation model with particle beam characteristics based on the calculated particle range and optionally on a calculated dose depth distribution; d) applying a single pencil beam shot to the determined target volume at an elevated beam energy as compared to the particle beam characteristics of the radiation model; e) measuring the beam range of the single pencil beam shot downstream of the determined target volume; and f) comparing the measured beam range to a reference beam range calculated on the basis of the radiation model.

8 Claims, 6 Drawing Sheets

U.S. PATENT DOCUMENTS

| | | |
|---|---|---|
| 7,560,715 B2 | 7/2009 | Pedroni |
| 7,659,521 B2 | 2/2010 | Pedroni |
| 7,682,078 B2 | 3/2010 | Rietzel |
| 7,931,784 B2 * | 4/2011 | Medoff .................... 204/157.63 |
| 2008/0071131 A1 | 3/2008 | Rietzel |
| 2010/0074408 A1 | 3/2010 | Bert et al. |
| 2011/0155559 A1 * | 6/2011 | Medoff .................... 204/157.63 |

FOREIGN PATENT DOCUMENTS

| | | |
|---|---|---|
| EP | 1911493 A1 | 4/2008 |
| EP | 1871477 B1 | 3/2011 |
| WO | 2004026401 A1 | 4/2004 |
| WO | 2008116596 A1 | 10/2008 |
| WO | 0102176 A1 | 1/2011 |

OTHER PUBLICATIONS

Pedroni, et al: "The 200-MeV Proton Therapy Project at the Paul Scherrer Institut: Conceptual Design and Practical Realization", 2389 Medical Physics, XP000505145, Jan. 1995, pp. 37-53, Woodbury, New York, USA.

* cited by examiner

METHOD FOR EVALUATING RADIATION MODEL DATA IN PARTICLE BEAM RADIATION APPLICATIONS

BACKGROUND OF THE INVENTION

Field of the Invention

The present invention relates to a method for evaluating radiation model data in particle beam radiation applications.

Particle therapy, in particular proton therapy, is an advanced method of applying cancer radiotherapy by using proton beams. It is a superior but costlier alternative to conventional therapy, which is usually applied with photon beams. Gantries for this kind of proton therapy have been published and proposed in the international patent applications WO 2001/00276 and WO 2004/026401 and in the European patent application 04 017 266.0 respectively.

In characterizing the distinction between photon beam therapy and proton beam therapy it has to be emphasized that a photon beam penetrates through the whole patient body. The dose profile is characterized by a dose maximum at about 1 cm under the skin followed by a monotonic exponential fall-off of the dose as a function of the depth. Unlike a photon beam, a proton beam is characterized by a well-defined range of penetration of the beam with a dose maximum at the end of the range, the so-called Bragg peak. By changing the energy of the proton beam the position of the Bragg peak in the interior of the patient body can be easily controlled.

Therefore, there exist several convincing reasons for using proton therapy instead of photon therapy. Due to the well-defined localization of Bragg peaks in depth, proton therapy can provide in almost any situation a better localization of the dose to the target volume as compared to conventional therapy with photons. With this method a better sparing of the healthy tissues surrounding the tumor can be achieved. This important issue is used in difficult clinical situations, mainly when the cancer is surrounded by sensitive anatomical structures. The higher magnetic rigidity of the proton beam requires the use of bulky equipment for the accelerator and for the beam lines, which makes on the other hand this superior therapy more expensive than conventional therapy.

Modern radiotherapy is preferentially delivered on the patient lying in supine position by applying the beam from different directions using a so-called gantry. Photon gantries span a diameter of only 2 to 3 m. A proton gantry is typically 10 m long, it comprises a proton beam line mounted on a heavy rigid support (with a total weight of more than 100 tons). The rotation of the proton gantry around the patient table spans a cylindrical volume with a radius of 3 to 6 m.

Another issue of practical interest in proton therapy is the possibility to deliver the beam by using an active dynamic beam delivery, beam scanning. The scan is performed with a small proton pencil beam (with a width of <1 cm), by applying magnetic deflections to the beam in the lateral direction and by changing dynamically the beam energy to vary the proton range. The dose is literally painted to any shape in three dimensions by touching with the Bragg peak spot (delivering variable local dose through time exposure or beam intensity changes) sequentially each point on a grid within the target (conformation of the dose to the target volume).

The scanning method must be compared with the more conventional method, which is to scatter the proton beam ahead of the patient table in order to obtain a homogeneous proton flow in the solid angle covering the tumor site. The shaping of the dose is then done in the lateral direction by using collimators and in depth by using passive ridge filters or other active modifiers like a rotating range shifter wheel (creation of a spread out Bragg peak SOBP through a spatial or time varying amount of material placed in the beam).

With proton beam scanning one can achieve a better conformation of the dose to the target volume. One can avoid the unnecessary 100% dose applied to the healthy tissue in reason of the fixed modulation of the range of the passive scattering method (constant SOBP compared to the variable SOBP of scanning, which can be varied as a function of the lateral position of the beam). The shaping of the dose is controlled completely just by computer control. There is no need to fabricate and position in the beam individually shaped hardware (the field and patient specific devices like collimators and compensators). With scanning the beam can be applied on the patient from several beam directions in sequence, without the need for the personnel to enter the treatment room (higher patient throughput to reduce costs can be achieved).

With scanning the dose distribution can be shaped to any shape, including (intentional) non-homogeneous dose distributions (with scattering a homogeneous dose is delivered by default). This possibility is the prerequisite for the delivery of the so-called intensity modulated proton therapy (IMPT), which relies on the idea to optimize the intensities of each proton pencil beam of a whole treatment all together independently of the gantry angle (simultaneous optimization of the beam spots). The constituent dose fields applied from each beam direction don't need to be homogeneous, only the sum must.

Currently, the proton gantry of the Paul Scherrer Institute at 5232 Villigen PSI in Switzerland (Proton therapy facility; its first beam line is there commonly known as "Gantry 1") is the first, and still the only, proton facility in the world capable of delivering therapy with an active scanning of the proton beam and capable of providing patient treatments with IMPT plans on a routine basis. In the context of the expansion of the PSI facility, an improved gantry for beam scanning ("Gantry 2") is currently under construction.

However, also with the new gantry various problems in dose shaping and exact dose delivery have to be solved. One of these problems is the challenge of organ motions due to various reasons. Organ motion during treatment is therefore a severe problem faced by any kind of precision radiotherapy (including dynamic therapy with photons). In case that during the delivery of the scanned beam the target volume moves, the shape and the homogeneity of the dose distribution can be significantly disturbed, up to the point that the dynamic beam delivery can not be used at all. This is actually a main criterion for the choice of the cases treated on the Gantry 1 of PSI. Due to the organ motion problem presently at PSI only non-moving tumors attached to bony structures are treated with the beam scanning method.

A significant improvement can be achieved by increasing the speed of scanning such that the target can be repeatedly scanned (target repainting, rescanning). This has been a major point of development for the new Gantry 2 and is established accordingly. The methods envisaged to cope with the organ motion problem in the presence of large movements like in the chest, are to switch off the beam, when the target is moved away from the desired position (gated beam delivery) or to follow directly with the pencil beam the displacement of the target (tracking). The best-known example of gating is the synchronization of the beam delivery within a given phase interval of the respiration cycle measured by external means (chest wall movement, control of the amount of inspired air etc.). The disadvantage of these methods is that the information on the target motion remains an indirect indication.

A Determined solution for this problem is disclosed in the European Patent Application EP 1 871 477 A1. This document discloses a system for an intensity-modulated proton therapy of a predetermined target volume within an object, comprising:
a) a proton source in order to generate a proton beam;
b) a number of proton beam bending and/or focusing units;
c) a beam nozzle having an outlet for the proton beam to penetrate the predetermined target volume of the object, thereby defining a cross sectional scanning exit area;
d) a beam bending magnet being disposed upstream of the nozzle;
e) an x-ray tube and an x-ray imager wherein the x-ray tube is associated with an irradiation channel within the beam bending magnet; said irradiation channel being oriented along the prolongation of the nominal proton beam direction thereby delivering the x-ray beam along the proton beam direction.

This solution which provides high precision and reliability for observing directly target motion and facilitating the option for applying tracking or gating onto a tumor optionally with marked with clips, is benefiting from the use of pulsed X-rays (i.e. shooting at a few Hz). It is therefore possible to work along all three objectives (rescanning, gating and tracking).

Nevertheless, another significant problem is still present related to accuracy of the proton delivery since even as protons have a well defined range determined by the position of the Bragg peak, the calculation of the range in the patient is of critical importance. This is particularly true as any errors in the calculated range are very probably systematic in character, and therefore won't necessarily smooth out over fractionation. One main determinant of the accuracy of proton range in the patient is the quality of the Computer Tomography (CT) or Magnetic Resonance (MR) data used for the calculations and the calibration curve converting CT Hounsfield Units or any equivalent thereof to proton stopping power. Although the calibration currently used in treatment planning systems has been validated against "biological" test samples, currently no method exists in order to verify proton ranges in-vivo. Given the importance of proton range as a parameter in the proton therapy as a parameter, a simple and easy measurement of the in-vivo range would be a tremendous step forward.

BRIEF SUMMARY OF THE INVENTION

It is therefore the objective of the present invention to provide a method for verifying the range of a particle beam in-vivo.

This objective is achieved according to the present invention by a method for evaluating radiation model data in particle beam radiation applications, in particular in proton beam therapy of a determined target volume of malign tissue within a human being, comprising the steps of:
a) gaining diagnostic data for a determined target volume to be irradiated;
b) calculating a particle range in the predetermined target volume based on the diagnostic data for the determined target volume;
c) designing a radiation model comprising particle beam characteristics based on the calculated particle range and optionally on a calculated dose depth distribution;
d) applying a single pencil beam shot to the determined target volume at an elevated beam energy as compared to the particle beam characteristics of the radiation model such as to exit the patient on the other side.
e) measuring the beam range of the single pencil beam shot downstream of the determined target volume; and
f) comparing the measured beam range to a reference beam range calculated on the basis of the radiation model.

In this way, a concept of a proton range probe is realized. The beam that passes completely through a patient allowing to measure the integral Bragg peak and/or its fall-off. Knowing the initial beam energy of the pencil beam "probe" allows to compare the measured result to the range applied for the calculation of the radiation model and to improve the accuracy of the CT and the calibration.

A preferred embodiment of the present invention provides the step of calculating the particle range on the basis of a calibration curve converting CT Hounsfield Units to particle stopping power. Of course, the result of the comparison in step f) may be used for an amendment of the calibration curve in case the result exceeds a predefined threshold.

A further preferred embodiment of the present invention provides the step of determining the location of the intrusion point of the single pencil beam shot depending on the inhomogeneities of the determined volume. Therefore, it is possible to achieve a bias curve for the particle range when using trajectories comprising more or less inhomogeneities than a mean reference trajectory, for example a trajectory traversing a cranium orthogonally to the bones of the cranium calvarium without interfering with other inhomogeneities, such as the bones of the otorhinolaryngologic section on the facial side of the cranium.

Occasionally, it can be rather difficult to determine the measured particle range due to some blurring effects. Therefore, a preferred embodiment provides in addition or alternatively a measurement of the beam range including or exclusively of the Bragg peak's fall-off of the single pencil beam shot.

A suitable resolution for the determination of the particle range is achievable when measuring the beam range at a spatial resolution of less than 10 mm, preferably less than 5 mm. Suitable detectors are of the wide area type, such as a multi-layer parallel plate detector.

Preferred embodiment of the present invention is described hereinafter more detailed with reference to the drawing which depict in.

BRIEF DESCRIPTION OF THE SEVERAL VIEWS OF THE DRAWING

DESCRIPTION OF THE INVENTION

Figure 1:
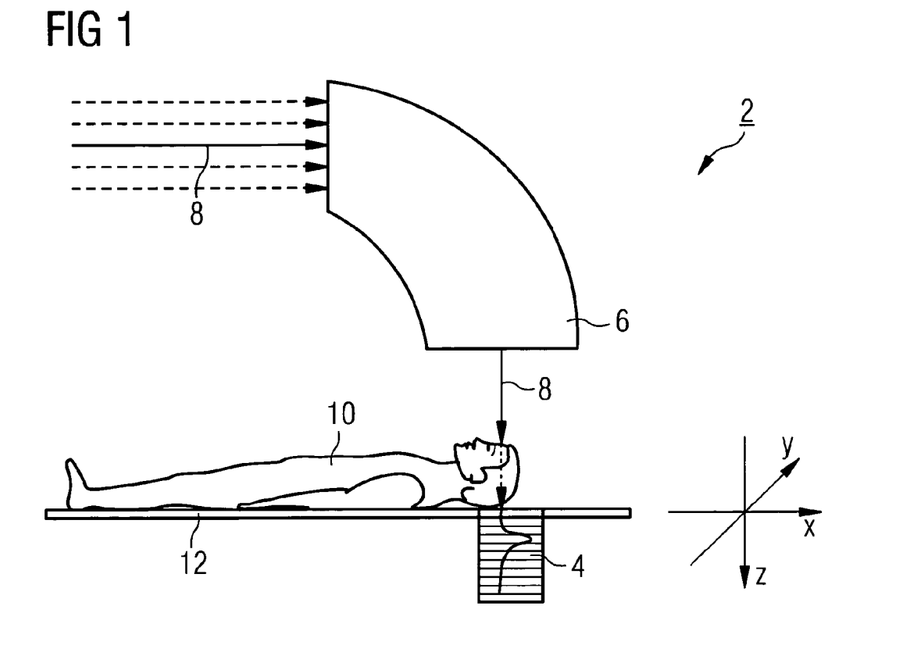
FIG. 1 a schematic view on a proton gantry comprising a multi-layer parallel plate detector.

FIG. 1 illustrates schematically a section of a proton gantry 2 comprising a multi-layer parallel plate detector 4. For the section of the proton gantry 2 a last 90° bending magnet 6 is illustrated which guides a proton beam 8 parallel to a z-axis towards a patient 10 being disposed on a patient table 12. For further details on the design of the proton gantry 2 and the delivery of a proton therapy with an active scanning of the proton beam 8 and capable of providing patient treatments with IMPT plans reference is made to the prior art documents mentioned above which are herewith incorporated by reference.

Downstream of the patient 10 as seen in the direction of the proton beam 8 the multi-layer parallel plate detector 4 is located. The detector 4 is designed as a multi-layer Faraday cup having a spatial resolution along the z-axis of about 2.5 mm.

The present embodiment therefore facilitates the concept of a proton "probe range" in order to get a feedback on the accuracy of the radiation plan derived from a conversion of CT Hounsfield Units into proton stopping power. Presently, a single proton pencil beam shot 8 is applied to the patient 10. The energy for proton beam for this shot is selected carefully under consideration of the proton range according to the radiation plan (which has its Bragg peaks within the patient's tissue) in order to be at an elevated level insuring that the proton beam 8 traverses completely through the patient 10 and having its Bragg peak within the range of the detector 4. This Bragg peak is exemplarily illustrated in the detector 4. The knowledge of the initial energy of the pencil beam "probe" can be converted into a proton range in water. The measurement of the Bragg peak outside the patient 10 within the range of the detector 4 further facilitates the determination of the residual range of the protons and therefore the amount of water equivalent material through which they have passed. By simulating the same probe (patient target volume) on the basis of the patient CT data (which has to be done anyway for the determination of the radiation plan) and comparing the simulation to the measurement, the accuracy of the CT Hounsfield Unit conversion and the calibration can be easily estimated. The results of this comparison are therefore most valuable information on the amendment necessarily to be made in order to approximate the conversion and calibration characteristics to the in-vivo measurement results. Of course, similar measurements can be also performed using an Alderson RANDO® phantom which behaves almost perfectly equivalent to the radiation absorption characteristic of human beings.

Figure 2:
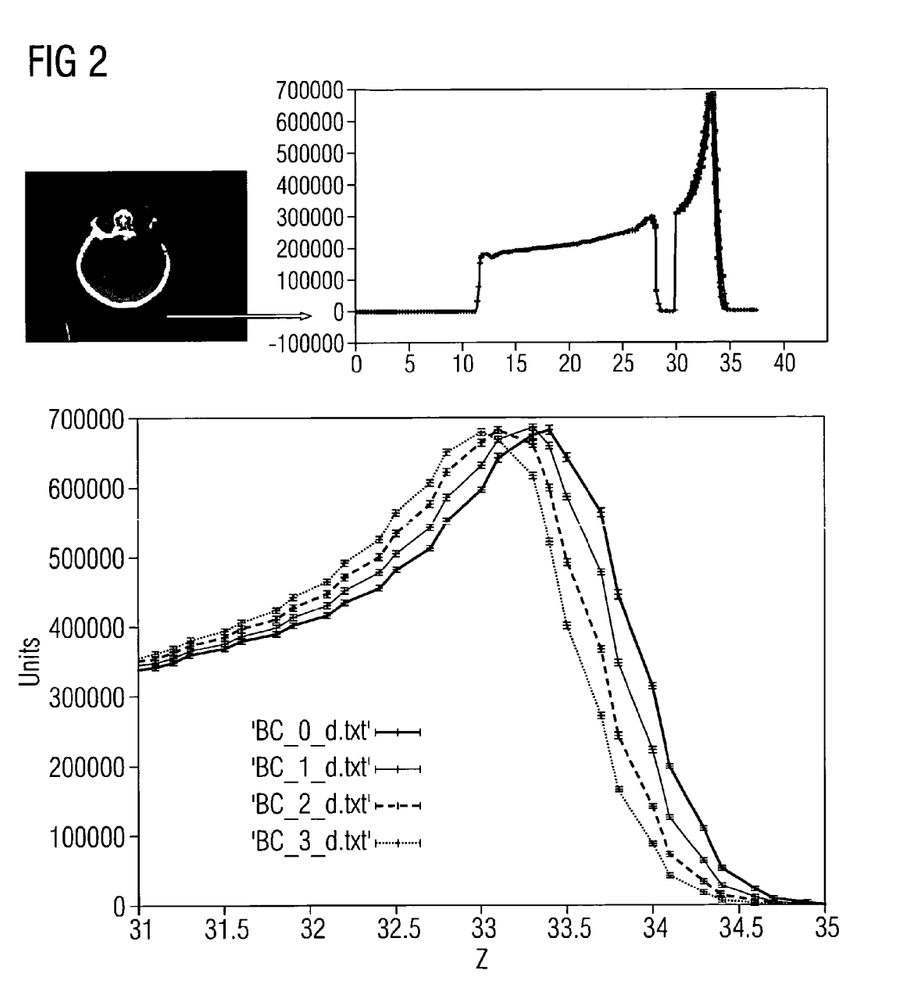
FIG. 2 a multiple of graphs showing the depth-dose distributions simulated for different models of Hounsfield Units for a rather homogeneous cranium trajectory.
Figure 3:
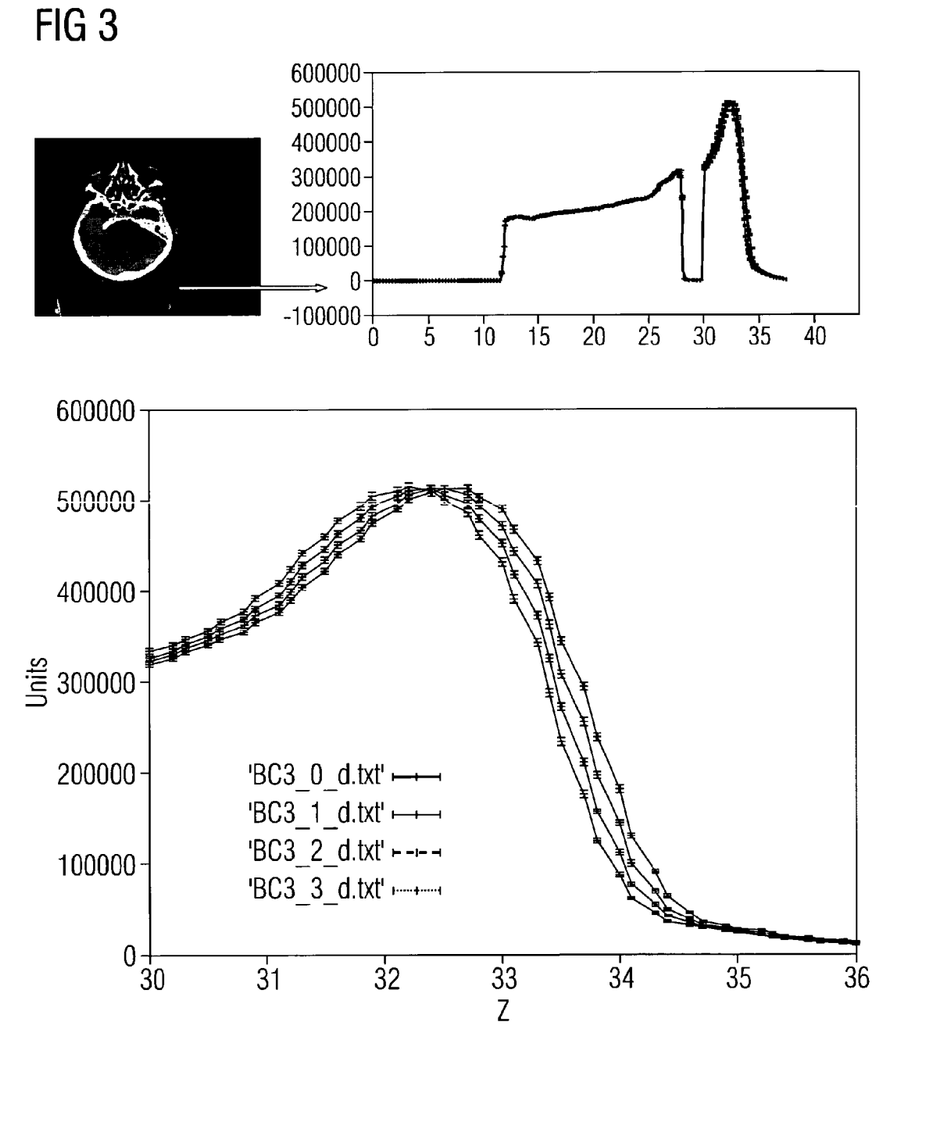
FIG. 3 a multiple of graphs showing the depth-dose distributions simulated for different models of Hounsfield Units for a rather homogeneous cranium trajectory but comprising additional bones as compared to FIG. 2.
Figure 4:
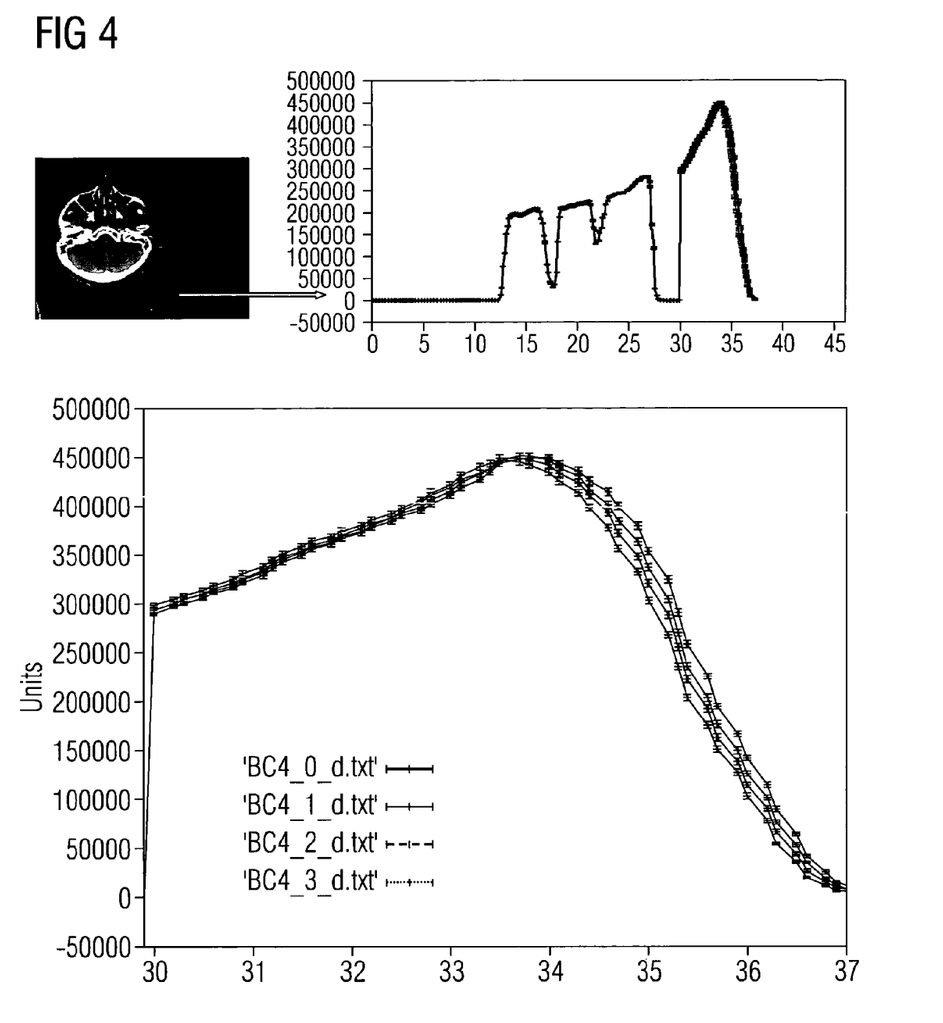
FIG. 4 a multiple of graphs showing the depth-dose distributions simulated for different models of Hounsfield Units for a rather homogeneous cranium trajectory but comprising additional bones and air cavities as compared to FIG. 3.

FIGS. 2 to 4 now illustrates each a multiple of graphs showing the depth-dose distributions simulated for different models of Hounsfield Units. In each figure, four graphs are shown. The graphs representing the depth-dose distributions for a non-changed CT image of the patient 10, for a CT with Hounsfield Unit (HU) change of 1%, 2% and 3% respectively. The x-axis is the range of the proton in cm and the y-axis is the dose in arbitrary units. FIG. 2 has been taken for a rather homogeneous cranium trajectory as illustrated in the CT image above the graphs. FIG. 3 was simulated for a rather homogeneous cranium trajectory but comprising additional bones as compared to FIG. 2 and FIG. 4 was simulated for a less homogeneous cranium trajectory but comprising additional bones and air cavities as compared to FIG. 3. Main qualitative observation from the comparison of the graph within the Figures and among the FIGS. 2 to 4 are that the changing of the Hounsfield Unit conversion model change the proton range but the form of the depth dose distribution is kept. The biggest range differences are observed for the more homogeneous regions.

Therefore, with single measurements of the dose with the detector 4 in slices perpendicular to the beam axis z, the form of the Bragg peak and the depth of the maximum of the Bragg peak can be determined which gives valuable information during the proton therapy to the question whether the patient is positioned correctly and to verify the calibration curve of the CT image which forms the basis for the determination of the radiation plan.

Figure 5:
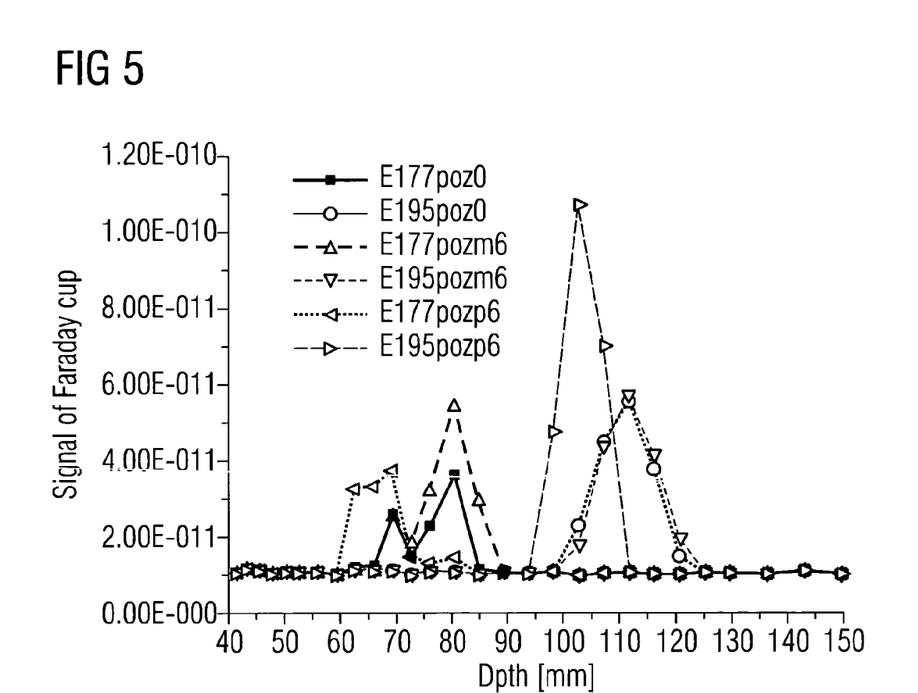
FIG. 5 a multiple of graphs showing the depth-dose distribution measured for two proton energies and three locations for each energy.

FIG. 5 depicts a multiple of graphs showing the depth-dose distribution measured for two proton energies (energy 177 MeV and 195 MeV and three locations for each energy (Location 0 "poz0", Location shifted by −6 mm "pozm6" and Location shifted by +6 mm "pozp6"). These measurements have been made using an Alderson cranium and recalculating the measurement for depth in water.

Figure 6:
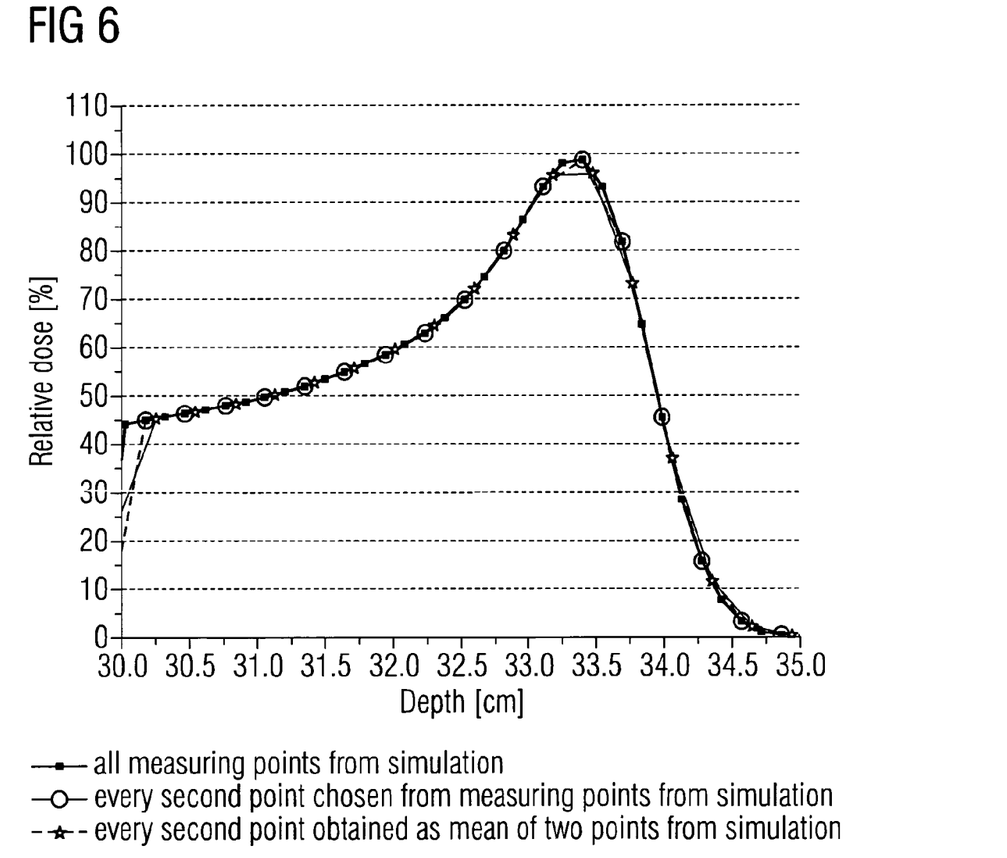
FIG. 6 a multiple of graphs in order identify the sensitivity of the spatial resolution when determining the range of the Bragg peak.

FIG. 6 illustrates a multiple of graphs in order identify the sensitivity of the spatial resolution when determining the range of the Bragg peak. The three graphs shows a substantial match though gained in different ways as explained on top of the chart.

Therefore, some further conclusions can be made on the resolution and the reliability of the measured data. First, for the Alderson Rando® phantom, the same tendencies as discussed with FIGS. 2 to 4 can be observed. With respect to the spatial resolution which is feasible at an industrial scale, the exact determination of the Bragg peak requires comparably high resolution in the range of less than 1 mm. The measurements have shown that the fall-off of the Bragg peak is more independent of the resolution of the measurements. For precise comparisons of proton ranges, the values for a range of 25 to 75% of the maximum dose have been approved of being advantageous. As a good pay-off between the resolution and the feasibility and cost of the detector when making conclusions on the basis of the range of the fall-off of the Bragg peak rather than on the range of the Bragg peak, a sensitivity of less than 1 cm is required for the resolution, preferably less than 5 mm.

Figure 7:
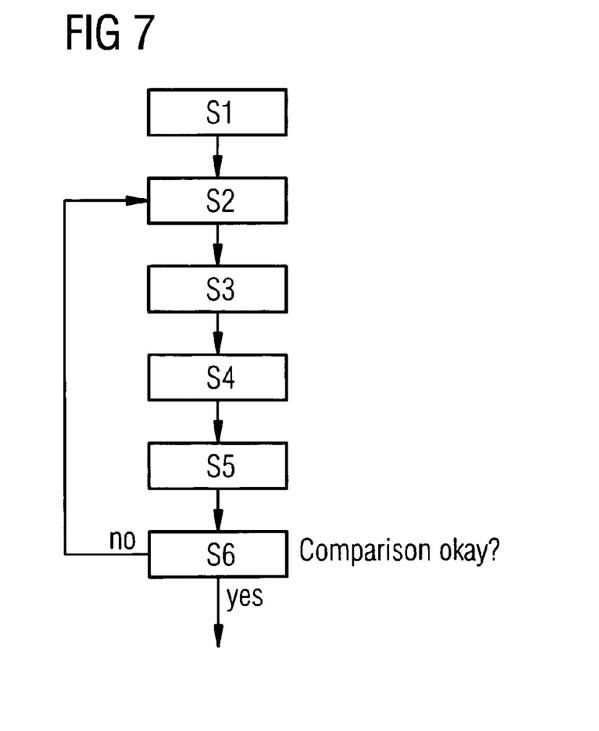
FIG. 7 the steps of a method for evaluating radiation model data in particle therapy applications.

FIG. 7 illustrates an embodiment of a method for evaluating radiation model data in particle therapy applications. The method comprises the following steps S1 to Sx:

Step S1: For a proton beam therapy of a determined target volume of malign tissue within a patient, initially diagnostic data, such as CT and/or MRI and/or US and/or photon diagnostic, has to be gained for the determined target volume to be irradiated.

Step S2: Based on the diagnostic data for the determined target volume a particle range is calculated in the predetermined target volume. For this calculation, for example, the CT Hounsfield Units are converted by a calibration curve to particle stopping power.

Step S3: A radiation model or radiation therapy plan comprising the particle beam characteristics specified for the target volume is designed based on the calculated particle range and optionally on a calculated dose depth distribution.

Step S4: A single pencil beam shot is applied to the human being at an elevated beam energy as compared to the particle beam characteristics of the radiation model.

Step S5: The beam range of the single pencil beam shot is measured downstream of the determined target volume; and Step S6: The measured beam range is compared to a reference beam range calculated on the basis of the radiation model.

This comparison enables the provider of the proton therapy to verify the current calculation basis of the radiation model. The results of the comparison forms actually the basis for a decision as to whether the current calculation basis has to be amended in order to match the calculated beam "behaviour" with the in-vivo gained behaviour. In case an adaptation has to be made, the method jumps back to Step S2 with a re-calculation of the proton range based on the amendments derived from the measured results. This re-calculation can be done for example by an adaptation of the Hounsfield conversion which is for example illustrated in FIGS. 2 to 4 where the graphs are shown for different Hounsfield Unit conversion grades.

The invention claimed is:

1. A method of evaluating radiation model data in a particle beam radiation application, the method which comprises
    a) gaining diagnostic data for a determined target volume to be irradiated;
    b) calculating a particle range in a predetermined target volume based on the diagnostic data for the determined target volume;
    c) designing a radiation model having particle beam characteristics based on the calculated particle range and optionally on a calculated dose depth distribution;
    d) applying a single pencil beam shot to the determined target volume at an elevated beam energy, elevated in comparison with the particle beam characteristics of the radiation model;
    e) measuring a beam range of the single pencil beam shot downstream of the determined target volume; and
    f) comparing the measured beam range to a reference beam range calculated on the basis of the radiation model.

2. The method according to claim 1, wherein the particle beam radiation application is a proton beam therapy of a determined target volume of malignant tissue within a patient.

3. The method according to claim 1, which comprises calculating the particle range on the basis of a calibration curve converting CT Hounsfield Units to particle stopping power.

4. The method according to claim 3, which comprises using a result of a comparison in step f) to amend the calibration curve in case the result exceeds a predefined threshold.

5. The method according to claim 1, which comprises determining a location of an entry point of the single pencil beam shot in dependence on the inhomogeneities of the determined volume.

6. The method according to claim 1, wherein the step of measuring the beam range includes measuring one or both of a Bragg peak and its fall-off of the single pencil beam shot.

7. The method according to claim 6, wherein the step of measuring the beam range is performed with a spatial resolution of less than 10 mm.

8. The method according to claim 7, which comprises measuring the beam range with a spatial resolution of less than 5 mm.

* * * * *